US00PP32662P2

(12) United States Plant Patent
Austin

(10) Patent No.: US PP32,662 P2
(45) Date of Patent: Dec. 22, 2020

(54) ***ROSA HYBRIDA* SHRUB PLANT NAMED 'AUSIMAGE'**

(50) Latin Name: *Rosa hybrida*
Varietal Denomination: AUSimage

(71) Applicant: David Austin Roses Ltd., Wolverhampton (GB)

(72) Inventor: David J. C. Austin, Wolverhampton (GB)

(73) Assignee: David Austin Roses Ltd., Albrighton (GB)

( * ) Notice: Subject to any disclaimer, the term of this patent is extended or adjusted under 35 U.S.C. 154(b) by 0 days.

(21) Appl. No.: 16/602,856

(22) Filed: Dec. 12, 2019

(51) Int. Cl.
*A01H 5/02* (2018.01)
*A01H 6/74* (2018.01)

(52) U.S. Cl.
USPC ..... Plt./107
CPC ..... *A01H 6/749* (2018.05)

(58) Field of Classification Search
USPC ..... Plt./107
CPC ..... A01H 6/749; A01H 5/02
See application file for complete search history.

*Primary Examiner* — Keith O. Robinson
(74) *Attorney, Agent, or Firm* — KPPB LLP

(57) ABSTRACT

A variety of rose plant of the shrub class, named 'AUSimage'. The 'AUSimage' is a variety of a rose shrub that produces a cut-flower rose having blush apricot colored, double blooms, which pale to cream on the outer petals, along with a good vase life and medium to strong fragrance.

1 Drawing Sheet

Classification: The present invention relates to a new *Rosa hybrida* shrub of the market class 'English Rose'.

Variety denomination: The new plant has the varietal denomination 'AUSimage'.

CROSS-REFERENCE TO RELATED APPLICATION

The present application claims priority to European Plant Variety Right 2019/2592, filed Oct. 11, 2019.

ORIGIN OF INVENTION

This invention relates to a new and distinct variety of shrub rose plant named 'AUSimage', which was originated from the cross-pollination of the two 'unnamed' and unpatented seedlings of *Rosa hybrida.*

BACKGROUND OF THE INVENTION

The primary objective of this breeding was to produce a cut-flower rose variety having blush apricot colored, double blooms, which pale to cream on the outer petals, along with a good vase life and medium to strong fragrance.

SUMMARY OF THE INVENTION

Among the features which distinguish the new variety from others presently available and commercial rose cultivars known to the inventor is the following combination of characteristics: blush apricot to peach center colored flowers with many petalled very large double blooms, strong stems, and a medium to strong myrrh fragrance.

Asexual reproduction of the new variety by budding as performed in Albrighton, Britain shows that the foregoing and other distinguishing characteristics come true to form and are established and transmitted through succeeding asexual propagations. 'AUSimage' may be asexually propagated by budding. The budding successfully occurred on an unpatented plant/rootstock *Rosa lnermis* for the observed plants.

COMPARISON WITH PARENTS

The maternal and paternal parents of 'AUSimage' are two unnamed seedlings. The new rose may be distinguished from its seed parent, by the following combination of characteristics: the seed parent has a flower which is pink in color with smaller, cupped blooms and is taller in habit compared to blush apricot flowers and large blooms of 'AUSimage'. The new rose may be distinguished from its pollen parent, by the following combination of characteristics: the pollen parent also has yellow colored blooms with extremely thorny growth and little to no fragrance compared to 'AUSimage' which has different colored blooms with fewer thorns and a stronger fragrance.

COMPARISON WITH THE CLOSEST COMMERCIALLY AVAILABLE CULTIVAR

The closest commercially available cultivar to the new variety is 'AUSboxer' (U.S. Plant Pat. No. 22,947). The bloom size of 'AUSboxer' is approx. 9 cm in diameter, large, so smaller than that of 'AUSimage' which is very large—12.5 cm. The petal count for 'AUSimage' is 90 petals, compared to 110 for 'AUSboxer'. There is a difference in the inner petal colour also—'AUSboxer' has petals of RHS 65B (pink group) with RHS 155D (white group) whereas 'AUSimage' is predominantly RHS 155B for the inner petals. The glossiness of the leaf blade can also be compared, with 'AUSboxer' exhibiting a glossy finish, and 'AUSimage' not glossy.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon The Colour Chart of The Royal Horticultural Society (2001) except where common terms of color definition are employed.

DESCRIPTION OF THE NEW VARIETY

Observations of budded 'AUSimage' specimens were made at a nursery in Albrighton, Wolverhampton, United Kingdom. The following description is of 5 year-old rose plants of the new variety grown in a greenhouse environment in Albrighton, Britain in the month of June. Phenotypic expression may vary with environmental, cultural and climatic conditions, as well as differences in conditions of light and soil.

FLOWER CHARACTERISTICS

Blooming habit: Continuous. The number of blooms per plant during the growing season is profuse, but there are too many to count.

Bud:

*Size*.—About 3 cm long and 2.5 cm in diameter when the petals start to unfurl.

*Form*.—The bud form is pointed ovoid.

*Color*.—When sepals first divide, the bud color is RHS 186B (grayed-purple group) tinged with RHS 10C (yellow group). When half blown, the upper sides of the petals are RHS N155D (white group), and the lower sides of the petals RHS 155C (white group).

*Calyx*.—Shape: star shape, with the sepals folding back against the stems. Length: 9.5 cm. Diameter: 9.5 cm.

*Sepals*.—Arrangement: Regularly arranged. Color: Upper Surface: RHS 144B (yellow-green group). Lower Surface: RHS 143A yellow-(green group) with RHS 60B (red-purple group) veining. Length: 4.2 cm. Width: 1.0 cm. Shape: Lanceolate. Surface texture: Upper Surface: Slightly hairy/downy. Lower Surface: Smooth. Number: There are 3 lightly appendaged sepals, and 2 unappendaged sepals with glandular edges. Sepal Extensions: Weak.

*Receptacles*.—Color: RHS 143C (green group). Shape: Pear. Size: Medium, about 1.0 cm long×1.3 cm wide. Surface: Smooth.

*Peduncle*.—Length: Short, averaging about 7.5 cm. Surface: Prickly. Color: RHS 151A (yellow-green group) with dapples of RHS 59A (red-purple group). Strength: Normal.

Blooms:

*Size*.—Very large, average open diameter is about 12.5 cm.

*Borne*.—Singly having a rounded shape.

*Stems*.—Strength: Strong, average length is about 100 cm. Diameter: 8-10 mm.

*Form*.—When first open, bloom is flat. Permanence of bloom: outer petal edges curl slightly.

*Flower type*.—Double.

Petalage: Number of petals under normal conditions: 90.

*Color*.—The upper sides of the petals are RHS 186D (grayed-purple group). The reverse sides of the petals are RHS N155D (white group). The base of the petals has a yellow shade basal spot RHS 2C (yellow group) on both inner and outer side.

*Variegations*.—None.

*Discoloration*.—The general tonality at the end of the first day is RHS 186D (grayed-purple group), and at the end of the third day is RHS N155D (white group).

*Fragrance*.—Moderate to strong. Character of fragrance: myrrh and aniseed.

Petals:

*Texture*.—Smooth and velvety.

*Size*.—Width: 4.4 cm. Length: 4.7 cm.

*Surface*.—Smooth/rough.

*Shape*.—Obovate.

*Margin*.—Very weak in terms of incisions/notches or undulations. Practically entire.

*Apex shape*.—Rounded.

*Base shape*.—Acute.

*Form*.—Slightly incurved.

*Arrangement*.—Irregular.

*Petaloids*.—Number: 6-7. Color: RHS N155B (white group). Length: 15 mm. Width: 7 mm. Shape: Obovate. Margin: Irregular.

*Persistence*.—Petals hang on and dry.

*Lastingness*.—On the plant: not tested. As a cut flower: about 11 days.

Reproductive parts:

*Stamens*.—Number: 35. Length: 13 mm.

*Anthers*.—Length: 3 mm. Color: RHS 15B (yellow-orange group). Arrangement: Mixed with petaloids.

*Filaments*.—Color: RHS 12B (yellow group). Length: 9 mm.

*Pollen*.—Color: RHS 15A (yellow-orange group). Amount: Scarce.

*Pistils*.—Number: 15. Length: 5 mm.

*Styles*.—Color: RHS 1D (green-yellow group). Length: 3-4 mm.

*Stigmas*.—Color: RHS 1B (green-yellow group). Length: 1 mm.

*Hips*.—NONE Observed.

PLANT CHARACTERISTICS

Plant form: Shrub.

Plant growth: Vigorous.

Age to maturity: 2 years.

Mature plant: Height: 100 cm. Width: 50-60 cm.

Rootstock: *Rosa lnermis* for the observed plants.

Foliage:

*Number*.—Leaflets on normal mid-stem leaves is: 5 with instances of 3 and 7 (including terminal leaflet).

*Size*.—Large, about 16.5 cm long×13.5 cm wide.

*Quantity*.—Normal. Number of leaves per flowering stem is: approx. 10.

*Color*.—New foliage: Upper side: RHS 143A (green group) edged with RHS 64A (red-purple group). Lower side: RHS 59B (red-purple group). Old foliage: Upper side: RHS N189A (grayed-green group). Lower side: RHS 138B (green group).

Leaflets:

*Size*.—About 7 cm long×5.3 cm wide.

*Shape*.—Pointed oval.

*Base shape*.—Cordate.

*Apex shape*.—Acuminate.

*Texture*.—Leathery.

*Glossiness*.—Medium to weak.

*Edge*.—Serrated.

*Serrations*.—Single.

*Petiole*.—Color: RHS 146D (yellow-green group). Length: 3 cm. Width: 0.5 mm. Surface Texture: Glandular but remaining smooth.

*Petiole rachis*.—Color: RHS 146B (yellow-green group). Underside: Rough.

*Stipules*.—Length: 2.5 cm, glandular. Color: RHS 146A (yellow-green group).

*Auricle*.—Shape: Not observed.

*Vein color*.—RHS N189A (grayed-green group).

*Venation pattern*.—Reticulate.

Wood:

*New wood*.—Color: RHS N144A (yellow-green group) with a touch of RHS 59A (red-purple group). Bark: Smooth.

*Old wood*.—Color: RHS 144A (yellow-green group). Bark: Smooth.

Branching habit:

*Number*.—N/A.

*Dimensions*.—N/A.

Stems:

*Mature stem*.—Length: 100 cm. Diameter: 8-10 mm.

*Internode distance*.—12 cm. The above measurements are all variable, depending on growing conditions in a season.

*Stem pubescence present*.—No.

Prickles:

*Quantity*.—On main canes from base: Ordinary. All prickles are very small — approximately 5 mm. Number per stem length: 3 per 10 cm.

*Form*.—Hooked downward.

*Length*.—5 mm.

*Color when young*.—RHS 182C (grayed-purple group) with hint of RHS 193A (grayed-green group).

*Color when mature*.—RHS 174B (grayed-orange group).

Small prickles:

*Quantity*.—Main stalk: Few. Number per stem length 3 per 10 cm.

*Color*.—When young: RHS 182C (grayed-purple group) with hint of RHS 193A (grayed-green group). When mature: RHS 174B (grayed-orange group).

Disease resistance:

*Powdery mildew* (*podosphaera pannosa*).—Resistant.

*Downy mildew* (*peronospora species*).—Resistant.

*Blackspot* (*diplocarpon rosae*).—N/A — not prevalent in greenhouse conditions.

*Rust* (*phragmidium tuberculatum*).—N/A — not prevalent in greenhouse conditions.

Pest resistance: Not tested.

Winter hardiness: Not tested.

Growing conditions: Normal greenhouse conditions.

What is claimed is:

1. A new and distinct variety of rose plant of the shrub class, substantially as herein shown and described.

* * * * *

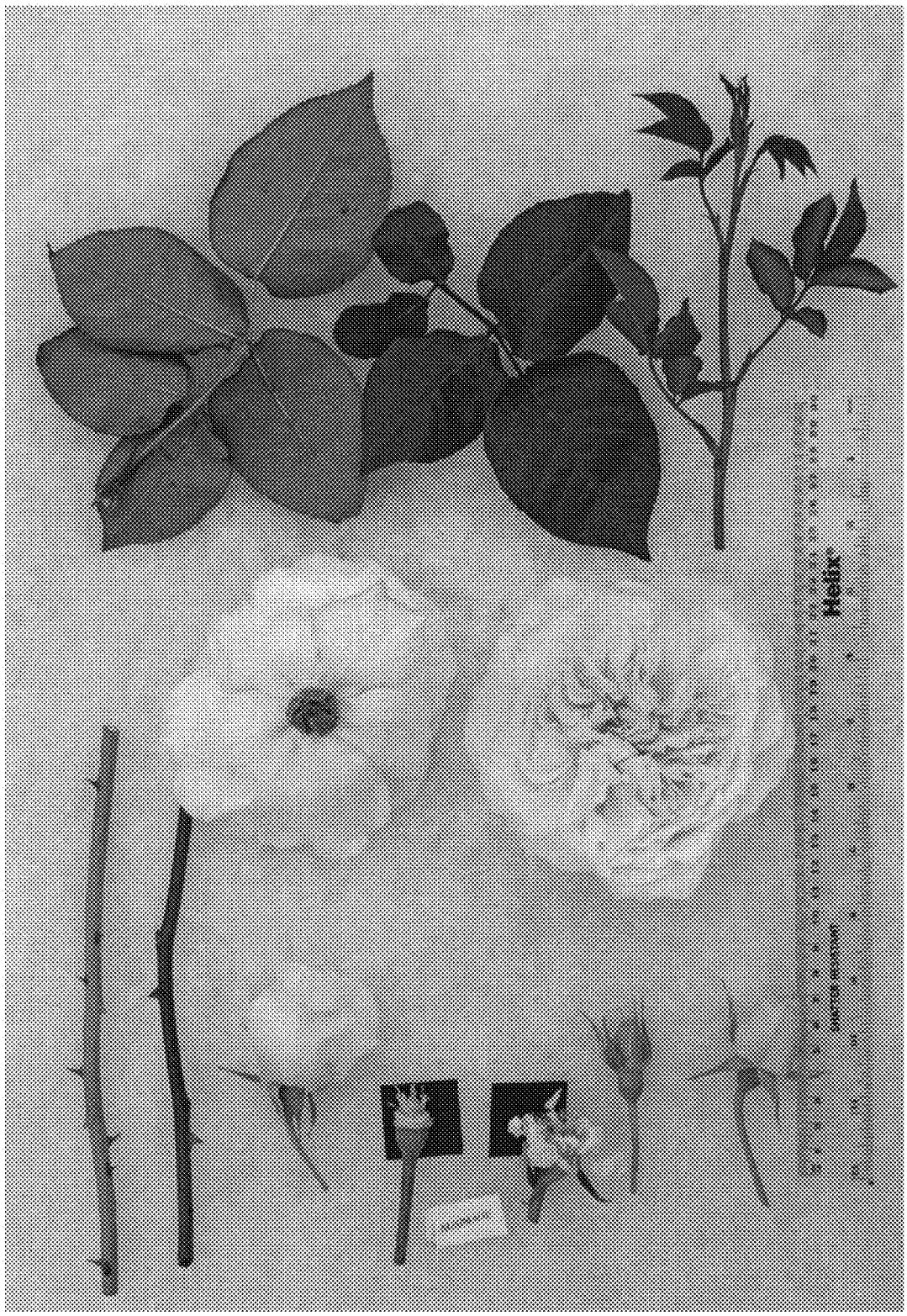
Felix